United States Patent [19]
Bige

[11] Patent Number: 6,152,916
[45] Date of Patent: Nov. 28, 2000

[54] BICANALICULAR PROBE FOR THE TREATMENT OF THE LACHRYMATION OF THE EYE

[76] Inventor: Pierre André Jacques Bige, 441 Chemin de Paramido, Port d'Alon, 83270 Saint Cyr sur Mer, France

[21] Appl. No.: 09/199,051

[22] Filed: Nov. 24, 1998

[30] Foreign Application Priority Data

Nov. 25, 1997 [FR] France ................... 97 14787

[51] Int. Cl.⁷ .................. A61B 17/00; A61M 5/00; A61F 11/00
[52] U.S. Cl. .................. 606/1; 604/8; 606/108
[58] Field of Search .............. 606/1, 108; 604/8

[56] References Cited

U.S. PATENT DOCUMENTS

| | | |
|---|---|---|
| 3,726,284 | 4/1973 | Parker ................... 128/350 |
| 4,305,395 | 12/1981 | Martinez ................... 128/348 |
| 4,753,637 | 6/1988 | Horneffer . |
| 5,052,998 | 10/1991 | Zimmon ................... 604/8 |
| 5,318,513 | 6/1994 | Leib et al. . |
| 5,437,625 | 8/1995 | Kurihashi ................... 604/8 |
| 5,501,232 | 3/1996 | Ritleng ................... 128/898 |
| 5,993,407 | 11/1999 | Moazed ................... 604/8 |

FOREIGN PATENT DOCUMENTS

| | | |
|---|---|---|
| 2735697 | 12/1996 | France . |
| 2 273 243 | 6/1994 | United Kingdom . |

*Primary Examiner*—Linda C. M. Dvorak
*Assistant Examiner*—Jocelyn Debra Ram
*Attorney, Agent, or Firm*—Leydig, Voit & Mayer, Ltd.

[57] ABSTRACT

A bicanalicular probe for the treatment of eye lachrymation including a filiform silicone element having free ends, each of which includes an anchor with flexible legs for retention of the filiform element at a junction of the lachrymal canaliculi and the lachrymal sac, the probe being particularly applicable in the treatment of canalicular stenosis.

8 Claims, 3 Drawing Sheets

PRIOR ART

BICANALICULAR PROBE FOR THE TREATMENT OF THE LACHRYMATION OF THE EYE

FIELD OF THE INVENTION

The present invention relates to a bicanalicular probe for the treatment of the lachrymation of the eye.

BACKGROUND

Various types of probes have already been proposed for treating the stenosis of the lachrymal passageways, i.e., marked obstruction of the lachrymal canaliculi and meati.

There are already known probes essentially consisting of a filiform element made from silicone which assumes the shape of a very fine tube and both ends of which are provided with a needle.

A needle is inserted through one of the two lachrymal meati up to and the nasal fossae by passing successively into one canaliculus, the lachrymal sac and the lachrymal-nasal duct and then the other needle is inserted into the other meatus up to and the nasal fossae by passing successively into a second canaliculus and then into the aforesaid lachrymal sac and lachrymal-nasal duct. Then both needles are separated from the tubular filiform element by cutting and both cut-off ends of this element are knotted together at the level of the nasal fossae.

Such a probe exhibits inconveniences in that it requires an intubation up to the nasal fossae, which is not at all necessary when one faces a pathology relating to the meati, both canaliculi and/or the duct connecting or joining both canaliculi leading to the lachrymal sac. Moreover the positioning of such a probe is relatively tricky, traumatizing for the patient and less well tolerated, let alone the fact that it must necessarily be implanted in a hospital or clinic.

SUMMARY OF THE INVENTION

The object of the present invention therefore is to remedy these inconveniences by proposing a bicanalicular probe of special and short structure which exhibits a minimum size and which restores the operation of the meati, of both canaliculi, and of the duct joining these two canaliculi to the lachrymal sac.

Moreover the probe according to this invention is very easily put in place, requires no intubation of the lachrymal-nasal duct, is better tolerated by the patient and may be put in place at the practioner's consulting room.

For that purpose, the subject of the invention is a bicanalicular probe for the treatment of the lachrymation of the eye, of the type comprising a filiform element made from silicone or other like material, both free ends of this element being provided with a means for retaining the filiform element at the level of the junction of the lachrymal canaliculi with the lachrymal sac.

According to a preferred embodiment, each retaining means is constituted by an anchor with at least two flexible legs.

It should be pointed out that the flexible legs of each anchor in the state of rest are turned towards the filiform element.

According to still another feature of this probe, each end of the filiform element forming the rod portion of the anchor is provided with a blind or recessed hole for receiving a rod or the like for operating the end.

The probe according to this invention has a filiform element between about 15 and 30 mm, and preferably between 20 and 22 mm, in length.

It should further be pointed out that the flexibility of the legs of each anchor is such that the legs are folded back upon the filiform element during the insertion of the probe and open or expand after having moved past the aforesaid junction opening into the lachrymal sac.

BRIEF DESCRIPTION OF DRAWING FIGURES

The invention will be better understood and further objects, details, characterizing features and advantages thereof will appear better as the following explanatory description proceeds with reference to the accompanying drawings given by way of example only and in which.

DETAILED DESCRIPTION

Figure 2:
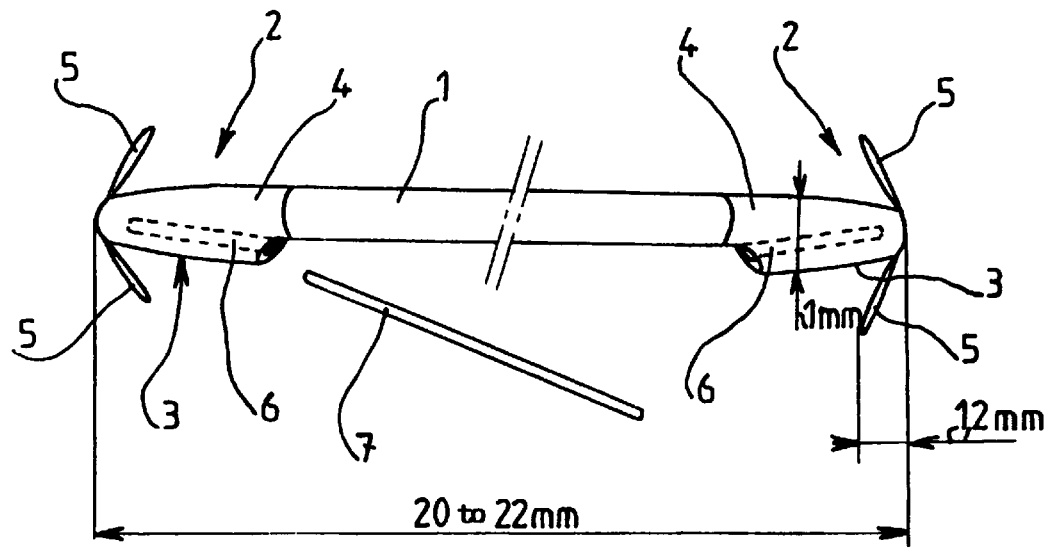
FIG. 2 is a side view of a bicanalicular probe according to the invention.
Figure 3:
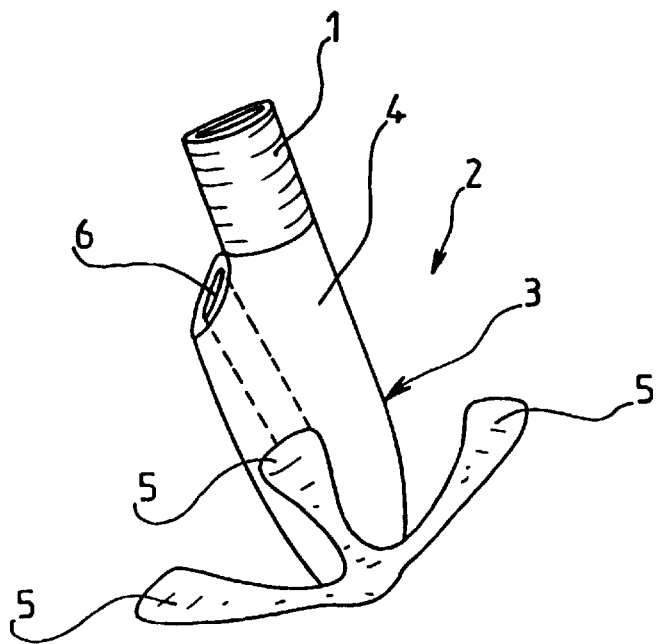
FIG. 3 is an enlarged perspective view of the anchor at each end of the probe.

According to the example shown on FIGS. 2 and 3, it is seen that a probe according to the principle of the invention consists of a filiform element 1 which may be a very fine tube made from silicone or other like material each of the free ends of which includes a retaining means 2.

As shown in FIG. 3, each retaining means 2 forms an anchor 3 comprising a rod-shaped portion 4 which carries at its end several flexible legs namely three or four legs according to the example shown. The rod-like portion 4 of the anchor 3 constitutes both ends of the filiform element or fine tube 1 made from silicone.

As clearly shown in FIGS. 2 and 3, in the state of rest of the probe, the flexible legs 5 are turned towards the filiform element 1.

Each end of this element 1, each rod-shaped portion 4 of the anchor 3, is provided with a blind or recessed hole 6 for receiving a rod or stem denoted 7 in FIG. 2. This rod or stem 7 operates the anchor-shaped end of the filiform element 1 for carrying out the placement of the probe as described further with reference to FIG. 4.

The length of the filiform element 1 is between about 15 and 30 mm. According to a preferred embodiment, this length will be between 20 and 22 mm.

The diameter of the silicone tube 1 can be 0.64 mm whereas the rod 7 may have a diameter of about 0.3 mm.

Figure 4:
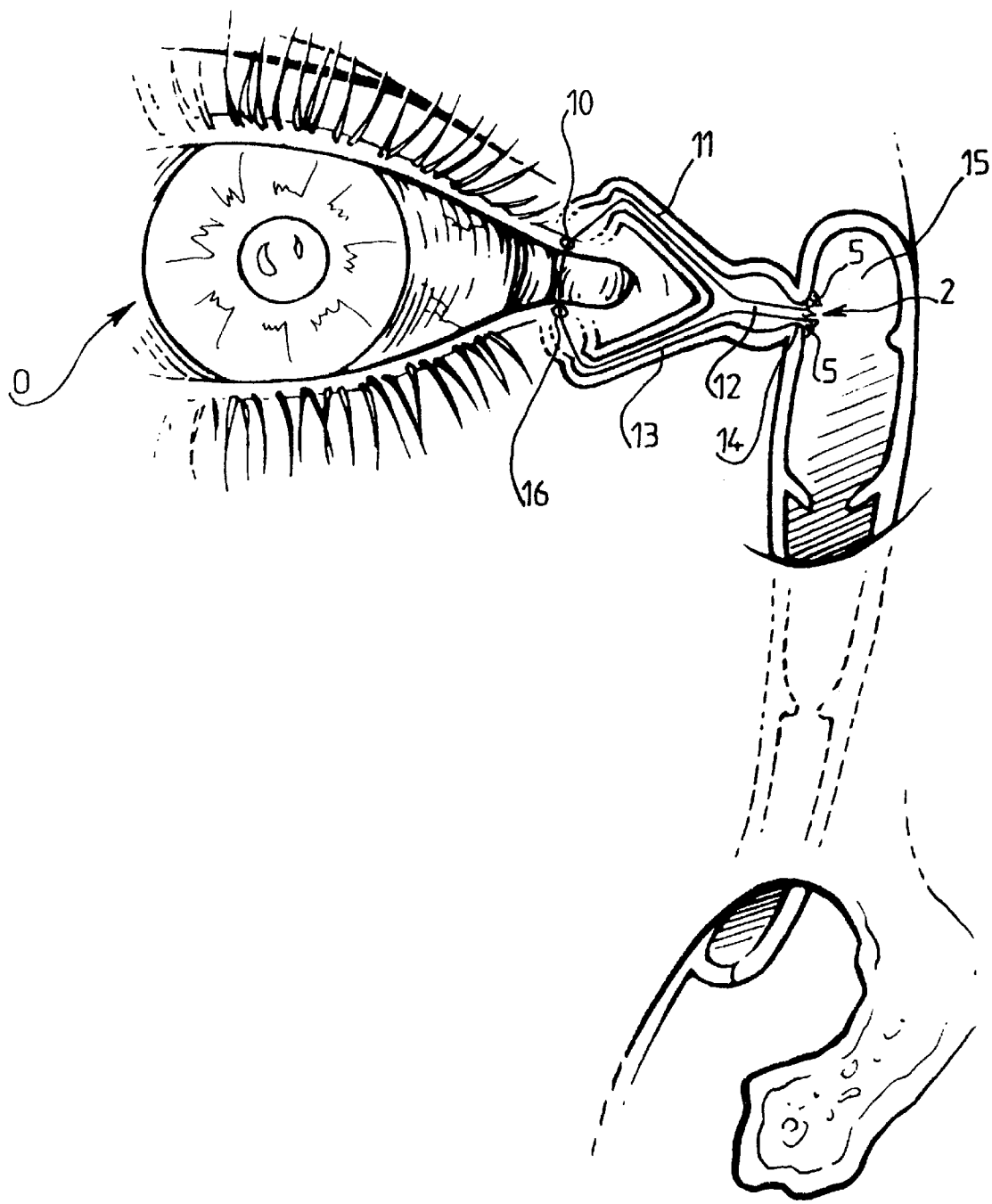
FIG. 4 is a view of the probe of the invention put in place in a patient.

The placement of the probe will now be described, and its advantages explained by referring to FIG. 4.

With the rod 7 being driven into one of the anchor-shaped ends 3 of the silicone tubular element 1, one would thus conveniently insert an anchor 3 into one of the two meati of the eye O, for example the upper meatus 10. It should be noted that during this insertion, the legs 5 of the anchor will easily move aside by folding themselves back upon the silicone tube 1. After having moved past the upper meatus 10, the anchor 3 would keep moving along its path by passing into the upper canaliculus 11 and then into the duct 12 connecting the upper canaliculus 11 to the lower canaliculus 13 for eventually moving past the junction 14 forming a valve between the connection duct 12 and the lachrymal sac 15. At this point, i.e., within the lachrymal sac 15, the flexible legs 5 would naturally unfold or extend and thus constitute a means for retaining or anchoring the probe at this level.

One should proceed in the same way as described above for inserting the other anchor 3, i.e., the other end of the filiform element 1 into the lower meatus 16. As previously described, this second anchor would successively pass into the lower canaliculus 13 and then into the connecting duct 12 for eventually moving past the junction 14, whereafter the flexible legs 5 would naturally unfold or become extended.

One therefore understands that both anchors 3 will retain the probe of the invention with its two ends at the level of the junction 14 of the lachrymal canaliculae 11, 13 at the lachrymal sac 15.

It should be specified here that not only the flexible legs of both anchors 3 will get caught on at the level of the junction 14 but these legs 5 will advantageously overlap with each other thereby providing a good retaining of the probe.

To proceed with the ablation of the probe, it will suffice to exert a slight pull thereupon so that the legs 5 of the anchors 3 in view of their flexibility will naturally escape or be released from the junction 14.

Figure 1:
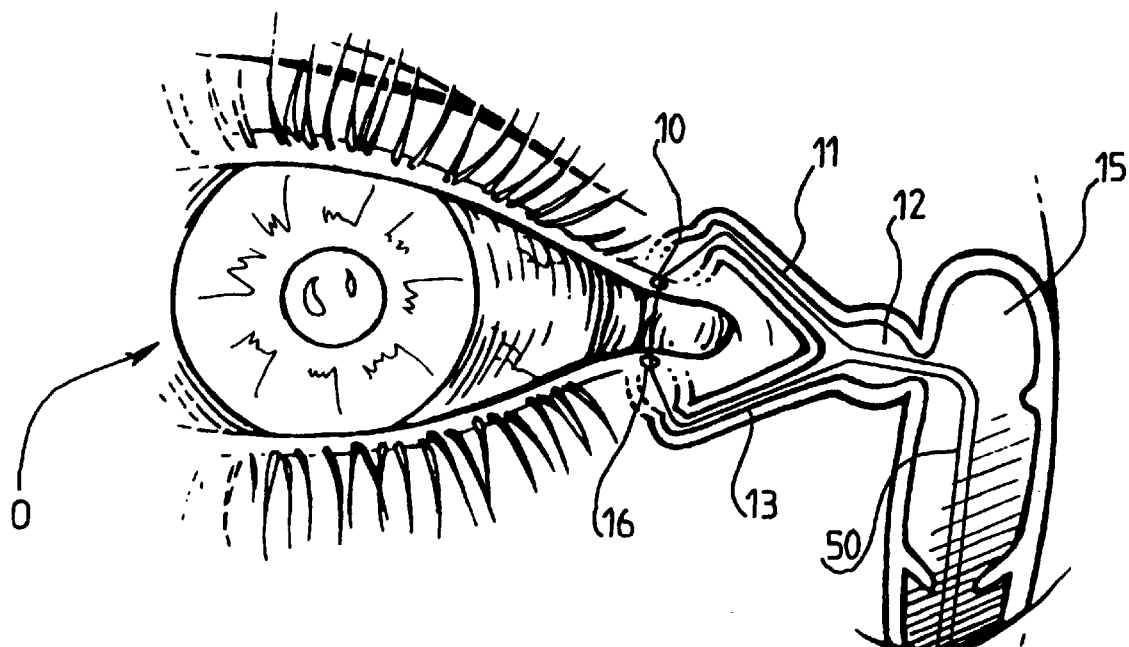
FIG. 1 is a view of a canalicular-nasal probe according to the prior art, implanted into a patient.
Figure 1:
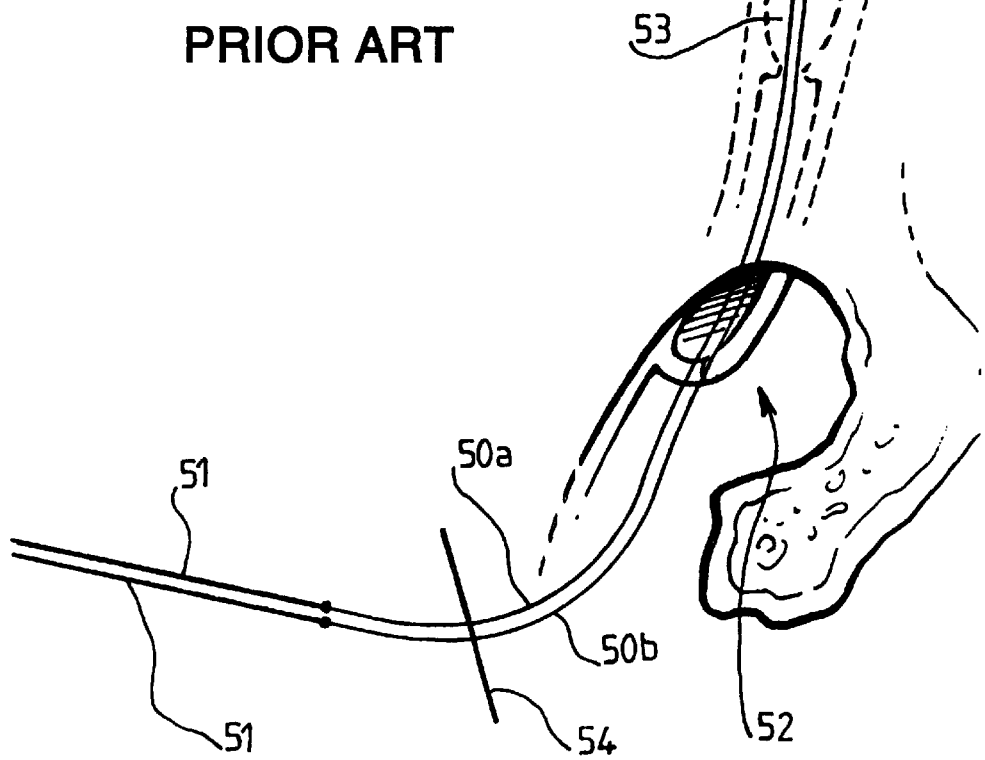

It is therefore understandable from the foregoing that the probe according to the invention does not require any bicanalicular intubation, i.e., a minimum intubation unlike the probes of the prior art such as the one shown on FIG. 1.

It is seen indeed in this figure as explained at the beginning of the present description that this known probe consists of a filiform silicone element 50 each of the ends comprising each one a needle 51 permitting the insertion of the probe through the upper meati 10 and 11 and up to the nasal fossae 52 after passage into the canaliculi 11, 13, into the connecting duct 12, into the lachrymal sac 15 and into the lachrymal-nasal duct. Once the probe has been inserted as seen in FIG. 1, the filiform element 50 is cut off as diagrammatically shown at 54 and one would make a knot is with both strands 50a, 50b of the filiform element separated from the needles 51, at the level of the nasal fossae 52, for, in a way, closing the loop. As explained at the beginning of the description, the placement of such a probe is more difficult, more traumatizing for the patient and less well tolerated.

Contrary to this, the probe according to the present invention is more physiological and easier to be used. It requires no intubation of the lachrymal-nasal duct and may be put in place quickly by a practitioner in his consulting room.

It should further be pointed out that the probe according to this invention permits remedying canalicular wounds after stitching, canalicular stenoses and those of the connecting duct, to the stenoses of the lachrymal meati and to the positioning defects of the meati which occur under the effect of the outwards reversal or eversion (ectropion) or inwards reversal or introversion (entropion) of the eyelids.

The invention is, of course, not at all limited to the described and illustrated embodiment of the probe which has been given by way of example only.

Thus the anchor-shaped ends of the tubular silicone element could be made as in one piece of material or through molding with the filiform element 1 or be secured and fastened onto this tubular element by any suitable means.

Therefore the invention comprises all the technical equivalents of the means described as well as their combinations if the latter are carried out according to its.

What is claimed is:

1. A bicanalicular probe for treatment of lachrymation of a human eye along a duct including lachrymal canaliculi and a lachrymal sac, the probe comprising a filiform element having two opposite free ends, wherein both free ends of the filiform element comprise means for retaining the filiform element at a junction of the lachrymal canaliculi and the lachrymal sac.

2. The probe according to claim 1, wherein each retaining means comprises an anchor with at least two flexible legs.

3. The probe according to claim 2, wherein the flexible legs of the anchor in a state of rest are turned towards the filiform element.

4. The probe according to claim 2, wherein each end of the filiform element comprises a rod portion of the anchor and has a recess for receiving a rod for operating the respective end.

5. The probe according to claim 1, wherein the filiform element has a length between about 15 and 30 mm.

6. The probe according to claim 2, wherein the flexible legs of each anchor fold themselves back upon the filiform element during insertion of the probe and unfold after having moved past the junction opening into the lachrymal sac.

7. The probe according the claim 5, wherein the length of the filiform element is between 20 and 22 mm.

8. The probe according to claim 1, wherein the filiform element is silicone.

* * * * *